United States Patent [19]

Hillemann

[11] Patent Number: 4,632,693

[45] Date of Patent: Dec. 30, 1986

[54] HERBICIDAL SULFONAMIDES

[75] Inventor: Craig L. Hillemann, Wilmington, Del.

[73] Assignee: E. I. Du Pont de Nemours and Company, Wilmington, Del.

[21] Appl. No.: 699,869

[22] Filed: Feb. 14, 1985

Related U.S. Application Data

[63] Continuation-in-part of Ser. No. 613,412, May 24, 1984.

[51] Int. Cl.$^4$ .................. A01N 43/66; C07D 251/42; C07D 251/16

[52] U.S. Cl. .......................................... 71/93; 544/211

[58] Field of Search ....................... 544/206, 208, 211; 71/93

[56] References Cited

U.S. PATENT DOCUMENTS 4,383,113  5/1983  Levitt .................................. 544/212

Primary Examiner—John M. Ford

[57] ABSTRACT

This invention relates to a novel herbicidal sulfonamide, agriculturally suitable compositions and a method for using it as an herbicide.

5 Claims, No Drawings

HERBICIDAL SULFONAMIDES

RELATED APPLICATIONS

This application is a continuation-in-part of U.S. Ser. No. 613,412 filed May 24, 1984.

BACKGROUND OF THE INVENTION

This invention relates to an herbicidally active sulfonamide, agriculturally suitable compositions thereof and a method for using it as an herbicide and/or plant growth regulant.

New compounds effective for controlling the growth of undesired vegetation are in constant demand. In the most common situation, such compounds are sought to selectively control the growth of weeds in useful crops such as cotton, rice, corn, wheat and soybeans, to name a few. Unchecked weed growth in such crops can cause significant losses, reducing profit to the farmer and increasing costs to the consumer. In other situations, herbicides are desired which will control all plant growth. Examples of areas in which complete control of all vegetation is desired are areas around fuel storage tanks, ammunition depots and industrial storage areas. There are many products commercially available for these purposes, but the search continues for products which are more effective, less costly and environmentally safe. The "sulfonylurea" herbicides are an extremely potent class of herbicides discovered within the last few years. A multitude of structural variations exist within this class of herbicides, but they generally consist of a sulfonylurea bridge, —$SO_2NHCONH$—, linking two aromatic or heteroaromatic rings.

The compound of this invention is within the generic disclosure in U.S. Pat. No. 4,383,113 which is directed to herbicidal benzenesulfonamides of the following formula:

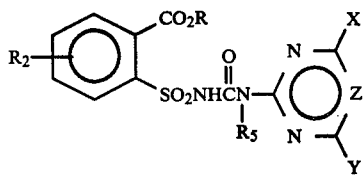

SUMMARY OF THE INVENTION

This invention is directed to the compound of the structural formula

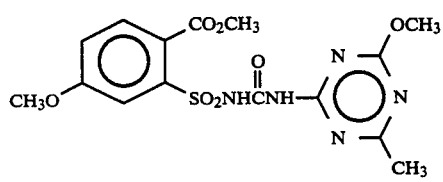

This invention is also directed to agriculturally suitable compositions of the compound of Formula I. Agriculturally suitable compositions for controlling the growth of undesired vegetation comprise an effective amount of a compound of structural Formula I and at least one of the following: surfactant, solid or liquid diluent.

This invention is also directed to a method of using the compound and/or compositions of the invention as a selective preemergent and/or postemergent herbicide by application to the locus of the crop to be protected.

The compound of structural Formula I is 4-methoxy-2-[[(4-methoxy-6-methyl-1,3,5-triazin-2-yl)-aminocarbonyl]aminosulfonyl]benzoic acid, methyl ester, m.p. 190°–192° C.

DETAILED DESCRIPTION OF THE INVENTION

Synthesis

The compound of Formula I can be prepared by the reaction of the sulfonyl isocyanate of Formula 1 with the triazin-2-amine of Formula 2 as shown in Equation 1.

Equation 1

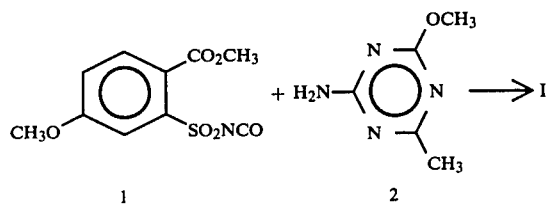

The reaction is best carried out in inert organic solvents such as dichloromethane, acetonitrile, tetrahydrofuran, dioxane, xylene or chlorobenzene, at temperatures between 20° to 100° C.

The sulfonyl isocyanate 1 can be prepared by methods described in U.S. Pat. No. 4,379,769. Amine 2 can be prepared by methods known to those skilled in the art.

Alternatively, the compound of Formula I can be prepared by the method shown in Equation 2.

Equation 2

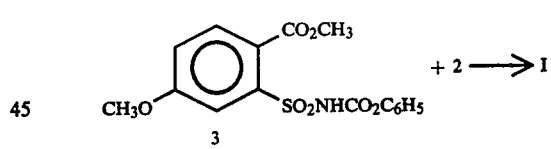

The reaction in Equation 2 is carried out by contacting the sulfonyl carbamate of Formula 3 with the amine 2 in an inert organic solvent such as dioxane or tetrahydrofuran at temperatures of about 20° to 100° C. for a period of 0.5 to 24 hours.

The carbamate 3 can be prepared by the methods described, or modifications thereof known to those skilled in the art, in European Patent Application 44,808 or South African Patent Application 82/5042.

The compound of Formula I may also be prepared by the procedure shown in Equation 3.

Equation 3

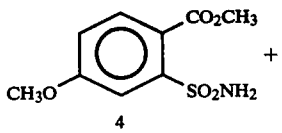

-continued
Equation 3

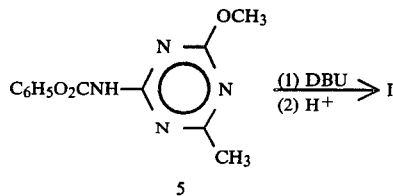

5

The reaction in Equation 3 is carried out by contacting equimolar amounts of sulfonamide 4 with the triazin-2-yl carbamate 5 in the presence of an equimolar amount of 1,8-diazabicyclo[5.4.0]undec-7-ene (DBU), analogous to methods described in South African Patent Application 83/0441. Carbamate 5 can be prepared by methods known in the art, e.g., South African Patent Applications 82/5671 and 82/5045.

Agriculturally suitable salts of the compound of Formula I are also useful herbicides and can be prepared in a number of ways known to the art. For example, metal salts can be made by contacting the compounds of Formula I with a solution of an alkali or alkaline earth metal salt having a sufficiently basic anion (e.g., hydroxide, alkoxide or carbonate). Quaternary amine salts can be made by similar techniques.

Salts of the compound of Formula I can also be prepared by exchange of one cation for another. Cationic exchange can be effected by direct contact of an aqeuous solution of a salt of the compound of Formula I (e.g., alkali or quaternary amine salt) with a solution containing the cation to be exchanged. This method is most effective when the desired salt containing the exchanged cation is insoluble in water and can be separated by filtration.

Exchange may also be effected by passing an aqueous solution of a salt of the compound of Formula I (e.g., an alkali metal or quaternary amine salt) through a column packed with a cation exchange resin containing the cation to be exchanged for that of the original salt and the desired product is eluted from the column. This method is particularly useful when the desired salt is water-soluble.

Acid addition salts, useful in this invention, can be obtained by reacting the compound of Formula I with a suitable acid, e.g., p-toluenesulfonic acid, trichloroacetic acid or the like.

The following examples illustrate the preparation of the compound of this invention.

EXAMPLE 1

Methyl 2[(dimethylamino)thioxomethoxyl]-4-methoxybenzoate

To a mixture of 350 g of methyl 2-hydroxy-4-methoxybenzoate, 648 g of 1,4-diazabicyclo[2.2.2]-octane (DABCO) and 3 L of dimethylformamide was added 712 g of dimethylthiocarbamoyl chloride. The mixture was warmed to 50° C. and held for 7 hours, then allowed to cool overnight. The mixture was poured into 10 L water; the aqueous mixture was extracted with 8 L of benzene-hexane (4:1). The organic solution was washed with 1N HCl, 10% NaOH, and dried over magnesium sulfate. Evaporation of the solvent in vacuo gave 396 g of the title compound, m.p. 95°–105° C. Further extraction of the aqueous mixture gave additional product, 171 g, m.p. 117°–120° C. Recrystallization of a portion of the crude product from methanol gave pure material, m.p. 122°–124° C.

EXAMPLE 2

Methyl 2-mercapto-4-methoxybenzoate

Under a nitrogen atmosphere, 935 g of the compound prepared in Example 1 was heated at 220° for 2.5 hours. The mixture was cooled to ambient temperature and added to a solution of 196 g of sodium methoxide in 3.5 L of methanol. The mixture was stirred 0.5 hours at 40°, refluxed 3.5 hours, then allowed to cool to ambient temperature. Removal of the solvent in vacuo gave a tan solid which was partitioned between 4 L of dichloromethane and 4 L of water. The aqueous phase was extracted twice with 500 ml dichlormethane, then acidified to pH 1.5 with dilute HCl. The oily mixture was extracted with dichloromethane. The organic phase was dried over magnesium sulfate, and the solvent evaporated in vacuo to give 475 g of the title compound as an oil which crystallized, m.p. 35°–37° C.

EXAMPLE 3

Sodium 4-methoxy-2-(methoxycarbonyl)benzenesulfonate

A mixture of 50 g of the compound of Example 2, 34 g of sodium formate and 505 ml of formic acid was warmed to 35° C. and 90 ml of 30% hydrogen peroxide was added slowly over 0.75 hours. The reaction temperature was allowed to warm to 55° C. and held at 55° C. for 2 hours. The reaction mixture was cooled to ambient temperature and 7 g of sodium sulfite was added in portions to destroy excess hydrogen peroxide. The reaction mixture was concentrated in vacuo at 50° C. Toluene (250 ml) was added to the residue, and the suspension was concentrated in vacuo. Repeating this procedure gave 109 g of the title compound as a moist white solid, m.p. >280° C.

EXAMPLE 4

Methyl 2-(chlorosulfonyl)-4-methoxybenzoate

To 500 ml of thionyl chloride was added portionwise over 1 hour 100 g of the compound of Example 3. The reaction mixture was stirred 0.5 hours, and 5 ml of dimethylformamide was added over 1 hour. The mixture was refluxed overnight. The orange solution was cooled to ambient temperature and concentrated in vacuo to a yellow semisolid. The reaction product was dissolved in 250 ml dichloromethane, and the solution was concentrated in vacuo. The resulting solid was partitioned between ether and water. The organic phase was washed with water, twice with aqeous sodium bicarbonate, dried over magnesium sulfate. Evaporation of the solvent in vacuo gave 47 g of the title compound, m.p. 69°–72° C.

EXAMPLE 5

Methyl 2-(aminosulfonyl)-4-methoxybenzoate

A solution of 554 g of the compound of Example 4 in 5 L of dichloromethane was cooled to −40° C. and 79 g of anhydrous ammonia was added at this temperature. The reaction mixture was allowed to warm to −10° C., stirred 1 hour, then poured into 6 L of water. The organic phase was separated and filtered. The filter cake was washed with dichloromethane and dried giving 356 g of crude product. A 180 g portion was recrystallized from methanol to give 130 g of the title compound, m.p. 139°–142° C.

Evaporation of the dichloromethane filtrate gave an additional 147 g, m.p. 135°–139° C.

EXAMPLE 6

Methyl 2-(isocyanatosulfonyl)-4-methoxybenzoate

A mixture of 100 g of the compound of Example 6, 40 g of n-butylisocyanate, 1 g of DABCO and 1500 ml xylene were refluxed 0.5 hours. Phosgene (63 g) was added over 4.5 hours while maintaining the reaction temperature >125° C. The mixture was heated 1.5 hours at 127° C., then allowed to cool to ambient temperature overnight under a nitrogen atmosphere. The reaction mixture was filtered and the filtrate was concentrated in vacuo to give 119 g of the title compound as an oil. IR (neat)—2250 cm$^{-1}$ (SO$_2$NCO).

EXAMPLE 7

Methyl 4-methoxy-2-[[(4-methoxy-6-methyl-1,3,5-triazin-2-yl)aminocarbonyl]aminosulfonyl]benzoate A solution of 119 g of the compound of Example 6 in 100 ml dichloromethane was added over 0.25 hours to a suspension of 57 g of 4-methoxy-6-methyl-1,3,5-triazin-2-amine in 1000 ml dichloromethane. The reaction was heated at reflux for 3 to 4 hours, then stirred overnight at ambient temperature. The reaction mixture was filtered and dried. The crude product was dissolved in 2000 ml boiling dichloromethane, the solution filtered, and the filtrate evaporated in vacuo to give 75 g of the title compound, m.p. 183°–186° C.

Formulations

Useful formulations of the compounds of Formula I can be prepared in conventional ways. They include dusts, granules, pellets, solutions, suspensions, emulsions, wettable powders, emulsifiable concentrates and the like. Many of these may be applied directly. Sprayable formulations can be extended in suitable media and used at spray volumes of from a few liters to several hundred liters per hectare. High strength compositions are primarily used as intermediates for further formulation. The formulations, broadly, contain about 0.1% to 99% by weight of active ingredient(s) and at least one of (a) about 0.1% to 20% surfactant(s) and (b) about 1% to 99.9% solid or liquid inert diluent(s). More specifically, they will contain these ingredients in the following approximate proportions:

TABLE 1

| | Active Ingredient | Weight Percent* Diluent(s) | Surfactant(s) |
|---|---|---|---|
| Wettable Powders | 20–90 | 0–74 | 1–10 |
| Oil Suspensions, Emulsions, Solutions, (including Emulsifiable Concentrates) | 3–50 | 40–95 | 0–15 |
| Aqueous Suspension | 10–50 | 40–84 | 1–20 |
| Dusts | 1–25 | 70–99 | 0–5 |
| Granules and Pellets | 0.1–95 | 5–99.9 | 0–15 |
| High Strength Compositions | 90–99 | 0–10 | 0–2 |

*Active ingredient plus at least one of a Surfactant or a Diluent equals 100 weight percent.

Lower or higher levels of active ingredient can, of course, be present depending on the intended use and the physical properties of the compound. Higher ratios of surfactant to active ingredient are sometimes desirable, and are achieved by incorporation into the formulation or by tank mixing.

Typical solid diluents are described in Watkins, et al., "Handbook of Insecticide Dust Diluents and Carriers", 2nd Ed., Dorland Books, Caldwell, N.J., but other solids, either mined or manufactured, may be used. The more absorptive diluents are preferred for wettable powders and the denser ones for dusts. Typical liquid diluents and solvents are described in Marsden, "Solvents Guide," 2nd Ed., Interscience, New York, 1950. Solubility under 0.1% is preferred for suspension concentrates; solution concentrates are preferably stable against phase separation at 0° C. "McCutcheon's Detergents and Emulsifiers Annual", MC Publishing Corp., Ridgewood, N.J., as well as Sisely and Wood, "Encyclopedia of Surface Active Agents", Chemical Publishing Co., Inc., New York, 1964, list surfactants and recommended uses. All formulations can contain minor amounts of additives to reduce foaming, caking, corrosion, microbiological growth, etc.

The methods of making such compositions are well known. Solutions are prepared by simply mixing the ingredients. Fine solid compositions are made by blending and, usually, grinding as in a hammer or fluid energy mill. Suspensions are prepared by wet milling (see, for example, Littler, U.S. Pat. No. 3,060,084). Granules and pellets may be made by spraying the active material upon preformed granular carriers or by agglomeration techniques. See J. E. Browning, "Agglomeration", *Chemical Engineering*, Dec. 4, 1967, pp. 147ff. and "Perry's Chemical Engineer's Handbook", 5th Ed., McGraw-Hill, New York, 1973, pp. 8–57ff.

For further information regarding the art of formulation, see for example:

H. M. Loux, U.S. Pat. No. 3,235,361, Feb. 15, 1966, Col. 6, line 16 through Col. 7, line 19 and Examples 10 through 41;

R. W. Luckenbaugh, U.S. Pat. No. 3,309,192, March 14, 1967, Col. 5, line 43 through Col. 7, line 62 and Examples 8, 12, 15, 39, 41, 52, 53, 58, 132, 138–140, 162–164, 166, 167 and 169–182;

H. Gysin and E. Knusli, U.S. Pat. No. 2,891,855, June 23, 1959, Col. 3, line 66 through Col. 5, line 17 and Examples 1–4;

G. C. Klingman, "Weed Control as a Science", John Wiley and Sons, Inc., New York, 1961, pp. 81–96; and J. D. Fryer and S. A. Evans, "Weed Control Handbook", 5th Ed., Blackwell Scientific Publications, Oxford, 1968, pp. 101–103.

In the following examples, all parts are by weight unless otherwise indicated.

EXAMPLE 8

| Wettable Powder | |
|---|---|
| 4-Methoxy-2-[[(4-methoxy-6-methyl-1,3,5-triazin-2-yl)aminocarbonyl]aminosulfonyl]-benzoic acid, methyl ester | 80% |
| sodium alkylnaphthalenesulfonate | 2% |
| sodium ligninsulfonate | 2% |
| synthetic amorphous silica | 3% |
| kaolinite | 13% |

The ingredients are blended, hammer-milled until all the solids are essentially under 50 microns, reblended, and packaged.

EXAMPLE 9

| Wettable Powder | |
|---|---|
| 4-Methoxy-2-[[(4-methoxy-6-methyl-1,3,5-triazin-2-yl)aminocarbonyl]aminosulfonyl]-benzoic acid, methyl ester | 50% |
| sodium alkylnaphthalenesulfonate | 2% |
| low viscosity methyl cellulose | 2% |
| diatomaceous earth | 46% |

The ingredients are blended, coarsely hammer-milled and then air-milled to produce particles essentially all below 10 microns in diameter. The product is reblended before packaging.

EXAMPLE 10

| Granule | |
|---|---|
| Wettable Powder of Example 9 | 5% |
| attapulgite granules (U.S.S. 20–40 mesh; 0.84–0.42 mm) | 95% |

A slurry of wettable powder containing 25% solids is sprayed on the surface of attapulgite granules while tumbling in a double-cone blender. The granules are dried and packaged.

EXAMPLE 11

| Extruded Pellet | |
|---|---|
| 4-Methoxy-2-[[(4-methoxy-6-methyl-1,3,5-triazin-2-yl)aminocarbonyl]aminosulfonyl]-benzoic acid, methyl ester | 25% |
| anhydrous sodium sulfate | 10% |
| crude calcium ligninsulfonate | 5% |
| sodium alkylnaphthalenesulfonate | 1% |
| calcium/magnesium bentonite | 59% |

The ingredients are blended, hammer-milled and then moistened with about 12% water. The mixture is extruded as cylinders about 3 mm in diameter which are cut to produce pellets about 3 mm long. These may be used directly after drying, or the dried pellets may be crushed to pass a U.S.S. No. 20 sieve (0.84 mm openings). The granules held on a U.S.S. No. 40 sieve (0.42 mm openings) may be packaged for use and the fines recycled.

EXAMPLE 12

| Oil Suspension | |
|---|---|
| 4-Methoxy-2-[[(4-methoxy-6-methyl-1,3,5-triazin-2-yl)aminocarbonyl]aminosulfonyl]-benzoic acid, methyl ester | 25% |
| polyoxyethylene sorbitol hexaoleate | 5% |
| highly aliphatic hydrocarbon oil | 70% |

The ingredients are ground together in a sand mill until the solid particles have been reduced to under about 5 microns. The resulting thick suspension may be applied directly, but preferably after being extended with oils or emulsified in water.

EXAMPLE 13

| Wettable Powder | |
|---|---|
| 4-Methoxy-2-[[(4-methoxy-6-methyl-1,3,5-triazin-2-yl)aminocarbonyl]aminosulfonyl]-benzoic acid, methyl ester | 20% |
| sodium alkylnaphthalenesulfonate | 4% |
| sodium ligninsulfonate | 4% |
| low viscosity methyl cellulose | 3% |
| attapulgite | 69% |

The ingredients are thoroughly blended. After grinding in a hammer-mill to produce particles essentially all below 100 microns, the material is reblended and sifted through a U.S.S. No. 50 sieve (0.3 mm opening) and packaged.

EXAMPLE 14

| Low Strength Granule | |
|---|---|
| 4-Methoxy-2-[[(4-methoxy-6-methyl-1,3,5-triazin-2-yl)aminocarbonyl]aminosulfonyl]-benzoic acid, methyl ester | 1% |
| N,N—dimethylformamide | 9% |
| attapulgite granules (U.S.S. 20–40 sieve) | 90% |

The active ingredient is dissolved in the solvent and the solution is sprayed upon dedusted granules in a double cone blender. After spraying of the solution has been completed, the blender is allowed to run for a short period and then the granules are packaged.

EXAMPLE 15

| Aqueous Suspension | |
|---|---|
| 4-Methoxy-2-[[(4-methoxy-6-methyl-1,3,5-triazin-2-yl)aminocarbonyl]aminosulfonyl]-benzoic acid, methyl ester | 40% |
| polyacrylic acid thickener | 0.3% |
| dodecylphenol polyethylene glycol ether | 0.5% |
| disodium phosphate | 1% |
| monosodium phosphate | 0.5% |
| polyvinyl alcohol | 1.0% |
| water | 56.7% |

The ingredients are blended and ground together in a sand mill to produce particles essentially all under 5 microns in size.

EXAMPLE 16

| Solution | |
|---|---|
| 4-Methoxy-2-[[(4-methoxy-6-methyl-1,3,5-triazin-2-yl)aminocarbonyl]aminosulfonyl]-benzoic acid, methyl ester | 5% |
| water | 95% |

The salt is added directly to the water with stirring to produce the solution, which may then be packaged for use.

EXAMPLE 17

| Low Strength Granule | |
|---|---|
| 4-Methoxy-2-[[(4-methoxy-6-methyl-1,3,5-triazin-2-yl)aminocarbonyl]aminosulfonyl]-benzoic acid, methyl ester | 0.1% |
| attapulgite granules | 99.9% |

-continued

| Low Strength Granule |
| --- |
| (U.S.S. 20–40 mesh) |

The active ingredient is dissolved in a solvent and the solution is sprayed upon dedusted granules in a double-cone blender. After spraying of the solution has been completed, the material is warmed to evaporate the solvent. The material is allowed to cool and then packaged.

EXAMPLE 18

| Granule | |
| --- | --- |
| 4-Methoxy-2-[[(4-methoxy-6-methyl-1,3,5-triazin-2-yl)aminocarbonyl]aminosulfonyl]-benzoic acid, methyl ester | 80% |
| wetting agent | 1% |
| crude ligninsulfonate salt (containing 5–20% of the natural sugars) | 10% |
| attapulgite clay | 9% |

The ingredients are blended and milled to pass through a 100 mesh screen. This material is then added to a fluid bed granulator, the air flow is adjusted to gently fluidize the material, and a fine spray of water is sprayed onto the fluidized material. The fluidization and spraying are continued until granules of the desired size range are made. The spraying is stopped, but fluidization is continued, optionally with heat, until the water content is reduced to the desired level, generally less than 1%. The material is then discharged, screened to the desired size range, generally 14–100 mesh (1410–149 microns), and packaged for use.

EXAMPLE 19

| High Strength Concentrate | |
| --- | --- |
| 4-Methoxy-2-[[(4-methoxy-6-methyl-1,3,5-triazin-2-yl)aminocarbonyl]aminosulfonyl]-benzoic acid, methyl ester | 99% |
| silica aerogel | 0.5% |
| synthetic amorphous silica | 0.5% |

The ingredients are blended and ground in a hammer-mill to produce a material essentially all passing a U.S.S. No. 50 screen (0.3 mm opening). The concentrate may be formulated further if necessary.

EXAMPLE 20

| Wettable Powder | |
| --- | --- |
| 4-Methoxy-2-[[(4-methoxy-6-methyl-1,3,5-triazin-2-yl)aminocarbonyl]aminosulfonyl]-benzoic acid, methyl ester | 90% |
| dioctyl sodium sulfosuccinate | 0.1% |
| synthetic fine silica | 9.9% |

The ingredients are blended and ground in a hammer-mill to produce particles essentially all below 100 microns. The material is sifted through a U.S.S. No. 50 screen and then packaged.

EXAMPLE 21

| Wettable Powder | |
| --- | --- |
| 4-Methoxy-2-[[(4-methoxy-6-methyl-1,3,5-triazin-2-yl)aminocarbonyl]aminosulfonyl]-benzoic acid, methyl ester | 40% |
| sodium ligninsulfonate | 20% |
| montmorillonite clay | 40% |

The ingredients are thoroughly blended, coarsely hammer-milled and then air-milled to produce particles essentially all below 10 microns in size. The material is reblended and then packaged.

EXAMPLE 22

| Oil Suspension | |
| --- | --- |
| 4-Methoxy-2-[[(4-methoxy-6-methyl-1,3,5-triazin-2-yl)aminocarbonyl]aminosulfonyl]-benzoic acid, methyl ester | 35% |
| blend of polyalcohol carboxylic esters and oil soluble petroleum sulfonates | 6% |
| xylene | 59% |

The ingredients are combined and ground together in a sand mill to produce particles essentially all below 5 microns. The product can be used directly, extended with oils, or emulsified in water.

EXAMPLE 23

| Dust | |
| --- | --- |
| 4-Methoxy-2-[[(4-methoxy-6-methyl-1,3,5-triazin-2-yl)aminocarbonyl]aminosulfonyl]-benzoic acid, methyl ester | 10% |
| attapulgite | 10% |
| pyrophyllite | 80% |

The active ingredient is blended with attapulgite and then passed through a hammer-mill to produce particles substantially all below 200 microns. The ground concentrate is then blended with powdered pyrophyllite until homogeneous.

EXAMPLE 24

| Emulsifiable Concentrate | |
| --- | --- |
| 4-Methoxy-2-[[(4-methoxy-6-methyl-1,3,5-triazin-2-yl)aminocarbonyl]aminosulfonyl]-benzoic acid, methyl ester | 20% |
| chlorobenzene | 74% |
| sorbitan monostearate and polyoxyethylene condensates thereof | 6% |

The ingredients are combined and stirred to produce a solution which can be emulsified in water for application.

EXAMPLE 29

| Oil Suspension | |
| --- | --- |
| 4-methoxy-2-[[(4-methoxy-6-methyl-1,3,5-triazin-2-yl)aminocarbonyl]aminosulfonyl]-benzoic acid, methyl ester | 35% |
| blend of polyalcohol carboxylic esters and oil soluble petroleum sulfonates | 6% |

| -continued | |
|---|---|
| Oil Suspension | |
| xylene | 59% |

The ingredients are combined and ground together in a sand mill to produce particles essentially all below 5 microns. The product can be used directly, extended with oils, or emulsified in water.

Utility

Test results indicate that the compound of the present invention is highly active as a preemergent and postemergent herbicide and as a plant growth regulant. The compound has utility for broad-spectrum pre- and postemergence weed control in areas where complete control of all vegetation is desired, such as around fuel storage tanks, ammunition depots, industrial storage areas, parking lots, drive-in theaters, around billboards, highway and railroad structures. The compound of this invention also has utility for selective weed control in crops such as wheat and barley. Compound I is particularly useful for the control of cheatgrass (*Bromus secalinus*), annual ryegrass (*Lobum multiflorum*), annual bluegrass (*Poa annua*), bedstraw (*Galium aparine*), speedwell (*Veronica persica*), and wild buckwheat (*Polygonum convovulus*). Alternatively, the subject compound is useful to modify plant growth.

The rate of application for the compound of this invention is determined by a number of factors, including its use as a plant growth modifier or as an herbicide, the crop species involved, the types of weeds to be controlled, weather and climate, formulations selected, mode of application, amount of foliage present, etc. In general terms, the subject compound should be applied at levels of around 0.004 to 2 kg/ha, the lower rates being suggested for use on lighter soils and/or those having a low organic matter content, for plant growth modification or for situations where only short-term persistence is required.

The compound of this invention may also be used in combination with any other commercial herbicide; examples of which are those of the triazine, triazole, uracil, urea, amide, diphenylether, carbamate and bipyridylium types.

The herbicidal properties of the subject compound was discovered in a number of greenhouse tests. The test procedures and results follow.

Test A

Seeds of crabgrass (Digitaris sp.), barnyardgrass (*Echinochloa crusgalli*), wild oats (*Avena fatua*), sicklepod (*Cassia obtusifolia*), morningglory (Ipomoea sp.), cocklebur (Xanthium sp.), sorghum, corn, soybean, sugar beet, cotton, rice, wheat and purple nutsedge (*Cyperus rotundus*) tubers were planted and treated preemergence with the test chemical dissolved in a nonphytotoxic solvent. At the same time, these crop and weed species were treated with a soil/foliage application. At the time of treatment, the plants ranged in height from 2 to 18 cm. Treated plants and controls were maintained in a greenhouse for sixteen days, after which all species were compared to controls and visually rated for response to treatment. The ratings, summarized in Table 1, are based on a numerical scale extending from 0=no injury, 10=complete kill. The accompanying descriptive symbols have the following meanings:

B=burn;
C=chlorosis/necrosis;
D=defoliation;
E=emergence inhibition;
F=growth retardation;
H=formative effects;
U=unusual pigmentation;
S=albinism; and
6Y=abscised buds or flowers.

TABLE 1

Compound

Compound 1

| Rate kg/ha | Cmpd. 1<br>0.05 |
|---|---|
| POSTEMERGENCE | |
| Morningglory | 10C |
| Cocklebur | 10C |
| Sicklepod | 9C |
| Nutsedge | 9G |
| Crabgrass | 3C, 8G |
| Barnyardgrass | 9C |
| Wild Oats | 9C |
| Wheat | 3C, 9G |
| Corn | 4U, 9G |
| Soybean | 5C, 9G |
| Rice | 5C, 9G |
| Sorghum | 3C, 9G |
| Sugar beet | 9C |
| Cotton | 10C |
| PREEMERGENCE | |
| Morningglory | 9C |
| Cocklebur | 9H |
| Sicklepod | 9G |
| Nutsedge | 10E |
| Crabgrass | 3C, 7G |
| Barnyardgrass | 5C, 9H |
| Wild Oats | 5C, 9G |
| Wheat | 5C, 9H |
| Corn | 4C, 9H |
| Soybean | 9H |
| Rice | 10E |
| Sorghum | 5C, 9H |
| Sugar beet | 10E |
| Cotton | 9H |

Test 2

Postemergence

Two round pans (25 cm diameter by 12.5 cm deep) were filled with Woodstown sandy loam soil. One pan was planted with blackgrass (*Alopecurus myosuroides*), sugar beets, nutsedge (*Cyperus rotundus*) tubers, crabgrass (*Digitaria sanguinalis*), sicklepod (*Cassia obtusifolia*), teaweed (*Sida spinosa*), jimsonweed (*Datura stramonium*), velvetleaf (*Abutilon theophrasti*), and giant foxtail (*Setaria faberii*). The other pan was planted with wheat, cotton, rice, corn, soybean, wild oats (*Avena fatua*), cocklebur (*Xanthium pensylvanicum*), morningglory (*Ipomoea hederacea*), johnsongrass (*Sorghum halepense*) and barnyardgrass (*Echinochloa crusgalli*). The plants were grown for approximately fourteen days, then sprayed postemergence with the compound of this invention dissolved in a non-phytotoxic solvent.

Preemergence

Two round pans (25 cm diameter by 12.5 cm deep) were filled with Woodstown sandy loam soil. One pan was planted with blackgrass, sugar beets, nutsedge, crabgrass, sicklepod, teaweed, jimsonweed, velvetleaf, and giant foxtail. The other pan was planted with wheat, cotton, rice, corn, soybeans, wild oats, cocklebur, morningglory, johnsongrass, and barnyardgrass. The two pans were sprayed preemergence with the compound of this invention dissolved in a non-phytotoxic solvent.

Treated plants and controls were maintained in the greenhouse for 28 days, then all treated plants were compared to controls and visually rated for plant response.

Response ratings are based on a scale of 0 to 10: where 0=no effect, and 10=complete control. The type of response is indicated by letters as described for Test 1. A dash (-) response means no test.

Response ratings are contained in Table 2.

TABLE 2

| | Compound 1 | | | | | | |
|---|---|---|---|---|---|---|---|
| | POSTEMERGENCE | | | | PREEMERGENCE | | |
| Rate g/ha | 62 | 16 | 4 | 1 | 250 | 62 | 16 | 4 |
| Corn | 10C | 7G | 5G | 2G | 10G | 10G | 8G | 5G |
| Wheat | 6G | 0 | 0 | 0 | 7G | 5G | 0 | 0 |
| Rice | 10C | 9G | 8G | 2G | 10G | 10G | 10G | 9G |
| Soybean | 10C | 10G | 9G | 5G | 10G | 10G | 9G | 7G |
| Cotton | 10C | 10C | 9G | 4G | 10G | 9G | 9G | 4G |
| Sugar beet | 10C | 10C | 10C | 6G | 10G | 10G | 10G | 9G |
| Crabgrass | 10G | 5G | 2G | 0 | 9G | 9G | 7G | 6G |
| Johnsongrass | 10C | 6G | 4G | 0 | 9C | 9C | 7G | 3G |
| Blackgrass | 10C | 10C | 9C | 5G | 10G | 10G | 10G | 8G |
| Barnyardgrass | 10C | 7G | 5G | 0 | 9G | 9G | 8G | 2G |
| Nutsedge | 10C | 5G | 0 | 0 | 10G | 10G | 9G | 8G |
| Giant Foxtail | 10C | 5G | 2G | 0 | — | — | — | — |
| Wild Oats | 10C | 8G | 4G | 0 | 9G | 9G | 6G | 3G |
| Cocklebur | 10C | 10C | 10C | 7G | 9G | 9G | 9G | 8G |
| Morningglory | 10C | 10G | 9G | 3G | 9G | 9G | 9G | 8G |

TABLE 2-continued

| | Compound 1 | | | | | | |
|---|---|---|---|---|---|---|---|
| | POSTEMERGENCE | | | | PREEMERGENCE | | |
| Rate g/ha | 62 | 16 | 4 | 1 | 250 | 62 | 16 | 4 |
| Teaweed | 10G | 7G | 3G | 0 | 9G | 9G | 9G | 5G |
| Sicklepod | 10C | 8G | 6G | 3G | 10G | 10G | 9G | 7G |
| Jimsonweed | 10C | 10C | 10C | 4G | 10G | 10G | 9G | 8G |
| Velvetleaf | 10C | 10C | 9G | 3G | 10G | 9G | 9G | 7G |

Test 3

Two ten-inch diameter plastic pans lined with polyethylene liners were filled with prepared Fallsington silt loam soil. One pan was planted with seeds of wheat (*Triticum aestivum*), barley (*Hordeum vulgare*), wild oats (*Avena fatua*), cheatgrass (*Bromus secalinus*), blackgrass (*Alopecurus myosuroides*), annual bluegrass (*Poa annua*), green foxtail (*Setaria viridis*), rapeseed (*Brassica napus*), and Italian ryegrass (*Lolium multiflorum*). The other pan was planted with seeds of Russian thistle (*Salsola kali*), speedwell (*Veronica persica*), kochia (*Kochia scoparia*), shepherd's purse (*Capsella bursa-pastoris*), *Matricaria inodora*, bedstraw (*Galium aparine*), black nightshade (*Solanum nigrum*), and wild buckwheat (*Polygonum convolvulus*). The above two pans were treated preemergence. At the same time two pans in which the above plant species were growing were treated postemergence. Plant height at the time of treatment ranged from 1–15 cm depending on plant species.

The compound was diluted in a nonphytotoxic solvent and sprayed over-the-top of the pans. An untreated control and a solvent alone were included for comparison. All treatments were maintained in the greenhouse for 20 days after which time the treatments were compared to the controls and the effects visually rated. The recorded data are presented in Table 3.

The duplicated entries for Compound 1 in Table 3 represent tests performed at different times of the year.

TABLE 3

| | Compound 1 | | | | | | | | | | |
|---|---|---|---|---|---|---|---|---|---|---|---|
| Rate kg/ha | 0.06 | 0.015 | 0.004 | .0009 | 0.06 | 0.015 | 0.004 | .0009 | 0.06 | 0.015 | 0.004 |
| Postemergence | | | | | | | | | | | |
| wheat | 2G | 1G | 0 | 0 | 2G,3C | 0 | 0 | 0 | 7G | 0 | 0 |
| barley | 9G | 7G | 4G | 4G | 8G,5C | 7G,5C | 4G | 0 | 10C | 9G | 7G |
| wild oats | 9G | 8G | 3G | 1G | 10C | 10C | 6G | 3G | 10C | 10C | 8G |
| cheatgrass | 9G,5C | 9G | 7G | 6G | 9G | 8G | 4G | 0 | 10C | 10C | 8G |
| blackgrass | 10C | 10C | 9G | 7G | 10C | 9G | 8G | 6G | 10C | 10C | 8G |
| annual bluegrass | 10C | 10C | 10C | 8G | 10C | 9G | 8G | 6G | 10C | 10C | 9G |
| green foxtail | 9G | 5G | 0 | 0 | 10C | 8G | 7G | 2G | 8G | 7G | 0 |
| Italian ryegrass | 10C | 10C | 9G | 7G | 10C | 10C | 10C | 8G | 10C | 10C | 10C |
| rapeseed | 10C | 10C | 10C | 10C | 10C | 10C | 10C | 10C | 10C | 10C | 10C |
| *Matricaria inodora* | 10C | 10C | 10C | 10C | 10C | 10C | 10C | 9G | 10C | 10C | 10C |
| *Galium aparine* | 10C | 10C | 10C | — | 6G | 5G | 2G | 0 | 10C | 10C | 10C |
| Russian thistle | 10C | 10C | 10C | 5G | 10C | 10C | 10C | 6G | 10C | 10C | 10C |
| shepherd's purse | 10C | 10C | 10C | 10C | 10C | 10C | 10C | 10C | 10C | 10C | 10C |
| kochia | 10C | 10C | 10C | 8G | 10C | 10C | 10C | 7G | 10C | 10C | 10C |
| black nightshade | 10C | 9G | 9G | 5G | 9G | 8G | 6G | 0 | 10C | 10C | 9G |
| speedwell | 10C | 10C | 9G | 10C | 10C | 10C | 10C | 10C | 10C | 10C | 10C |
| wild buckwheat | 10C | 10C | 10C | 0 | 10C | 10C | 9G | 7G | 10C | 10C | 9G |
| sugar beets | 10C | 10C | 10C | 10C | 10C | 10C | 10C | 10C | 10C | 10C | 10C |
| Preemergence | | | | | | | | | | | |
| wheat | 2G | 1G,3C | 0 | 0 | 6G | 2G | 0 | 0 | 1G | 0 | 0 |
| barley | 7G | 6G | 3G | 2G | 8G | 7G | 5G | 2G | 9G | 5G | 1G |
| wild oats | 7G,6C | 7G | 3G | 0 | 9G | 8G | 7G | 3G | 10C | 9G | 7G |
| cheatgrass | 10C | 9G,5C | 7G | 3G,5C | 8G | 8G | 6G | 3G | 10C | 10C | 10C |
| blackgrass | 9G,7C | 9G | 8G | 2G | 9G | 8G | 6G | 3G | 10C | 10C | 10C |
| annual bluegrass | 10C | 10C | 9G | 7G | 9G,7C | 9G | 8G | 3G | 10C | 10C | 10C |
| green foxtail | 4G | 7G,2C | 3G | 1G | 9G,3C | 5G | 2G | 0 | 9G | 8G | 1G |
| Italian ryegrass | 10C | 10C | 7G | 2G | 10C | 9G | 8G | 6G | 10C | 10C | 10C |
| rapeseed | 10C | 10C | 9G | 3G | 10C | 10C | 8G | 10C | 10C | 10C | 10C |
| *Matricaria inodora* | 10C | 9G | 9G | 9G | 10C | 9G | 9G | 10C | 10C | 10C | 10C |

TABLE 3-continued

| Rate kg/ha | Compound 1 | | | | | | | | | | |
|---|---|---|---|---|---|---|---|---|---|---|---|
| | 0.06 | 0.015 | 0.004 | .0009 | 0.06 | 0.015 | 0.004 | .0009 | 0.06 | 0.015 | 0.004 |
| *Galium aparine* | 10C | — | — | — | 10C | 9G | 9G | 8G | 10C | 10C | 10C |
| Russian thistle | 10C | 8G | 8G | 7G | 10C | 9G | 10C | 5G | 10C | 10C | 4G |
| shepherd's purse | 10C | 10C | 10C | 10C | 10C | 10C | 10C | 8C | 10C | 10C | 10C |
| kochia | 9G,7C | 9G | 9G | 2G | 10C | 10C | 9G | 7G | 10C | 10C | 10C |
| black nightshade | 9G,7C | 9G,5C | 9G,1C | 7G | 9G,5C | 9G,3C | 9G | 8C | 10C | 10C | 10C |
| speedwell | 10C | 10C | 10C | 10C | 10C | 10C | 10C | 10C | 10C | 10C | 10C |
| wild buckwheat | 9G | 9G | 8G,2C | 7G | 9C,3C | 9G | 9G | 8C | 10C | 10C | 10C |
| sugar beets | 10C | 10C | 10C | 10C | 10C | 10C | 10C | 10C | 10C | 10C | 10C |

What is claimed is:

1. An agriculturally suitable composition for controlling the growth of undesired vegetation postemergence in wheat comprising an effective amount of the compound of the formula

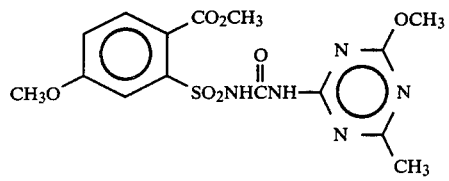

and at least one of the following: surfactant, solid or liquid diluent.

2. A method for controlling the growth of undesired vegetation which comprises applying to wheat postemergence an effective amount of the compound

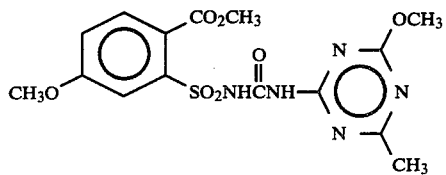

3. The method of claim 2 wherein the undesired vegetation is *Bromus secalinus*.

4. The method of claim 2 wherein the undesired vegetation is *Lolium multiflorum*.

5. The method of claim 2 wherein the undesired vegetation is *Poa annua*.

* * * * *